United States Patent [19]
Sherrod et al.
[11] 4,087,453
[45] May 2, 1978

[54] PROCESS FOR OBTAINING GLYCOLS AND GLYCERINE OR DI- AND TRIESTERS THEREOF FROM POLYGLYCOLS AND POLYGLYCERINE

[75] Inventors: Fred A. Sherrod, Freeport; William L. Howard; Joanne D. Burger, both of Lake Jackson, all of Tex.

[73] Assignee: The Dow Chemical Company, Midland, Mich.

[21] Appl. No.: 697,799

[22] Filed: Jun. 18, 1976

Related U.S. Application Data

[63] Continuation-in-part of Ser. No. 469,138, May 13, 1974, abandoned.

[51] Int. Cl.[2] ...................... C07C 29/00; C07C 31/20; C07C 31/22; C07C 67/24

[52] U.S. Cl. .................................... 560/240; 568/858; 560/263

[58] Field of Search .................... 260/496, 491, 488 J, 260/635 R

[56] References Cited

U.S. PATENT DOCUMENTS

| | | | |
|---|---|---|---|
| 2,030,835 | 2/1936 | Cox et al. | 260/488 |
| 2,629,735 | 2/1953 | Cottle et al. | 260/488 |

*Primary Examiner*—Vivian Garner
*Attorney, Agent, or Firm*—A. C. Ancona

[57] ABSTRACT

A process for recovering monomeric glycols and glycerine from polyoxyalkylene glycols and polyglycerines which comprises heating the polymeric compounds together with a lower saturated mono-carboxylic acid, containing from 2 to 4 carbon atoms such as acetic acid, in the presence of a strong acid, e.g. sulfuric acid, or a strong acid cation exchange resin. The product, which is the diester of the monomeric glycol or the triester of glycerine, is recovered and subsequently hydrolyzed to obtain the desired monoglycol or glycerine product. If it is desired to obtain the ester itself, the latter step of hydrolyzing can be omitted.

1 Claim, No Drawings

PROCESS FOR OBTAINING GLYCOLS AND GLYCERINE OR DI- AND TRIESTERS THEREOF FROM POLYGLYCOLS AND POLYGLYCERINE

CROSS-REFERENCE TO RELATED APPLICATION

This application is a continuation-in-part of prior application Ser. No. 469,138 filed May 13, 1974, now abandoned.

BACKGROUND OF THE INVENTION

The cleavage of ethers with organic acids has been known since the 1890's, for example dihydroxy maleic acid was employed in the presence of dry hydrogen bromide to cleave ethyl ether and form the diethyl ester of the acid. Oxalic, acetic, benzoic, stearic and boric acids were employed later in analogous reactions [J. Chem. Soc. 73, 554 (1898)]. Ethyl acetate and tertiary butyl alcohol were formed by cleaving tertiary butyl ethyl ether with acetic acid in the presence of a trace of sulfuric acid. This was reported as a special case because of the exceptionally high reactivity of the tertiary butyl radical [J. Am. Chem. Soc. 54, 2099 (1932)]. A year later Hennion, et al. reported the reaction of several ethers with various organic acids in the presence of boron trifloride to form esters. A more recent reference Die Makromolekulare Chemie, Vol. 54, 1962, p. 15) to a cleavage of glycols containing alkyl end groups, e.g. diethylene glycol diethyl ether, was found in which acetic anhydride was employed in the presence of boron trifluoride to produce a good yield of ethylene glycol diacetate.

While the cleavage of ethers on a laboratory scale and under certain specialized conditions appears possible, the conversions, yields, reactants or catalyst systems employed have not been conducive to the development of a commercially acceptable process. Either conversions or yields, or both have been inadequate, or the catalyst systems and reactants employed have been exotic and expensive. Thus, the cleavage of polyglycols and polyglycerine, by the present process provides a successful method suitable for commercial development.

In processes employed commercially to make glycols and glycerine there are appreciable amounts of higher polymeric etherlinked polyols formed. Although there are some limited uses for the polyglycols and polyglycerine, it would be highly desirable if these could be converted to the more useful monomeric glycols and glycerine. The present process provides just such a desired result.

SUMMARY OF THE INVENTION

It has now been discovered that the polyglycols and polyglycerine can be reacted with a lower saturated mono-carboxylic acid in the presence of a strong acid to form the di- and triesters of the monomeric glycols and glycerine, respectively; the acid catalyst is then separated or neutralized, and thereafter the esters of the monomeric glycols and glycerine can be separated from the reaction mixture; the glycol or glycerine can be recovered by hydrolyzing the esters produced. If the esters themselves are to be utilized as such, the final hydrolysis step can be omitted. Excellent yields approaching 100% are attainable.

The process can be made continuous by passing the carboxylic acid and polyol, preferably the polyol ester, through a column of a strong acid cation exchange resin in the acid form at a rate sufficient to produce the desired conversion, separating the desired esters of the monoglycol or glycerine, and, recycling the remaining materials back to the column after removal of water therefrom.

DETAILED DESCRIPTION OF THE INVENTION

According to the present invention polyoxyalkylene glycols and polyglycerine can be reacted with a lower saturated mono-carboxylic acid in the presence of a strong acid or a strong acid cation exchange resin to produce the diester of a monoalkylene glycol or the triester of glycerine. The reactants useful in the invention are the polyoxyalkylene glycols, such as ethylene, propylene and butylene polyglycols containing two or more alkylene units. Specific examples are diethylene glycol, triethylene glycol, tetraethylene glycol and higher polymers of ethylene glycol. Likwise the analogous propylene and butylene glycols may be used. Thus, dipropylene glycol, tripropylene glycol, tetrapropylene glycol and higher polypropylene glycols, dibutylene glycol, tri-butylene glycol, tetrabutylene glycol and higher polybutylene glycols may be employed.

The saturated carboxylic acids useful as reactants to form the esters are the lower saturated carboxylic acids such as acetic, propionic, and butyric. The acid catalytic agent employed in this reaction is a strong acid or a strong acid cation exchange resin in the acid form. A preferred strong mineral acid is sulfuric. Other strong acids having relatively high boiling points are also useful, e.g. arysulfonic acids such as benzenesulfonic acid, toluenesulfonic acid and naphthalenesulfonic acid. Cation exchange resins preferred are those of the sulfonated polystyrene type, e.g., those derived from sulfonated styrene-divinylbenzene copolymers. Commercially available resins of this type are Dowex 50, Amberlite IR-120, Lewatit S100, Diaion SK 112 and Wofatit KP 5200.* A further criterion for the strong acids and the acid form of the cation exchange resins which are useful as catalysts is that they have a $PK_a$ of 3 or less. The strong acid catalyst must be present in an amount greater than 4% by weight based on the total reactants; i.e., polyol and carboxylic acid. An equivalent amount of an acid form of a cation exchange resin is likewise required when such is substituted for the strong acid.

*These are tradenames for strong acid exchange resins of The Dow Chemical Co., Rohm & Haas Co., Farbenfabriken Bayer, Mitsubishi Chem. Ind, Ltd., and VEB Farbenfabric Wolfen, respectively.

The di- and triglycerines as well as high polyglycerines may by cleaved in like manner with a lower carboxylic acid to obtain the triesters of glycerine in good yields. Both the esters of the glycols and of glycerine may then be hydrolyzed to obtain the monoglycol or monglycerine molecule by known procedures.

GENERAL PROCEDURE

A reaction solution of the polyoxyalkylene compound, the appropriate saturated carboxylic acid and strong acid catalyst, in an amount greater than 4% by weight based on the polyoxyalkylene and carboxylic acid employed, were heated together in a flask fitted with a fractionating column. This column was equipped for control of the take-off valve in accordance with the head temperature. The control monitor was set slightly higher than the boiling point of water so that the distillate would consist mainly of water. Additional carboxylic acid was added as needed during the course of the reaction. This acid was added in a volume approximately equivalent to that of the liquid taken overhead. Reaction and distillation were continued until the overhead consisted essentially of the pure carboxylic acid. The control setting of the temperature monitor was raised incrementally toward the end of the reaction to the boiling point of the reactant acid to force the distillation of all the water. The strong acid catalyst was neutralized and the excess carboxylic acid was distilled off prior to recovery of the ester or, alternatively, prior to its hydrolysis.

In a preferred process the polyoxyalkylene glycol or polyglycerine is reacted with sufficient of the carboxylic acid to esterify the free hydroxyls, the water of reaction is distilled off, and the esterified polyol is then reacted with more of the carboxylic acid to obtain the esters of the monoglycol or glycerine. When a preliminary esterification of the free hydroxyl groups is to be accomplished prior to employing the polyol ester as a reactant in a continuous process over an ion exchange resin, the esterification requires only trace amounts of a strong acid, i.e., less than 1%, especially in the case of the esterification of polyglycerine as discussed hereafter.

In the case of the polyglycerine there are more than two free hydroxyls, so that more carboxylic acid is needed for the esterification of the free hydroxyls. There a tendency for the secondary hydroxyls of polyglycerine to split off in the presence of strong acid, forming water and producing unsaturation in the molecule. To avoid this it is desirable to esterify these secondary hydroxyls in the polyglycerine molecule by using, in addition to the acid necessary to esterify the primary hydroxyls, about one mole of carboxylic acid anhydride for each mole of secondary hydroxyl present.

The reaction mixture employed in a batch reaction should contain from about two to about 20 moles of carboxylic acid per mole of ether links in the polyol reactant, but preferably from about 4 to about 10. The temperature in the process is controlled by the boiling point of the carboxylic acid being used, but is generally at a temperature within the range of about 100° to 200° C, preferably 120°–170° C. Pressure above atmospheric may be employed, but is not necessary.

An alternate method is to employ as the catalyst the hydrogen form of a strong acid cation exchange resin in a column reactor and pass the polyol ester, i.e., the polyol having all hydroxyls esterified, together with the saturated mono-carboxylic acid through the column to accomplish the ether-splitting reaction to obtain the esters of the monoglycols or glycerine. The mixtures of esterified polyol and carboxylic acid is passed through the column at a temperature of from about 100° to 200° C and preferably 110° to 140° C. The higher temperatures are deleterious to the cation exchange resin, reducing its efficiency, and at temperatures below about 100° C the rate of cleavage becomes so slow as to be impractical.

The reaction mixture employed in the continuous reactor through a column of the cation exchange resin should contain from about one to about 20 moles of carboxylic acid per mole of ether links in the polyol reactant and preferably from about two to about 8.

The rate of throughput is such as to provide a contact time which will give the desired conversion of the polyol ester in the cleavage reaction.

The product mixture is distilled, or otherwise separated, to collect the desired glycol or glycerine esters and the remainder recycled to the process. Water, of course, must be removed from both the desired product and recycle materials.

SPECIFIC EXAMPLES

The following reactions were conducted according to the batch-type general procedures given above and are shown in Table I below. The percent yield was determined by a chromatographic method. All examples were conducted at atmospheric pressure. Conversion of the polyglycol was essentially 100% except as noted.

TABLE I

| Example | Polyol* | Amt. (g) | Acid | Amt. (g) | Catalyst | Percent** Catalyst | Time (hr) | Reactor Temp. (° C) | Yield (%) ## |
|---|---|---|---|---|---|---|---|---|---|
| 1 | DEG | 636 | Acetic | 1440 | $H_2SO_4$ | 4.8 | 29 | 119–38 | 90 |
| 2 | DEG | 318 | Acetic | 1280 | Dowex 50 | 10.8 | 10 | 119–38 | 90 |
| 3*** | DEG | 106 | Propionic | 543 | $H_2SO_4$ | 7.4 | | | 95 |
| 4 | TTEG | 388 | Acetic | 1200 | $H_2SO_4$ | 4.6 | 21 | 119–38 | 90 |
| 5 | E4000 | 132 | Acetic | 738.6 | $H_2SO_4$ | 4.4 | 59 | 119–38 | 80 |
| 6 | E4000 | 15 | Propionic | 151.5 | Dowex 50 | ca 50 | 4 | 125 | 71 |
| 7*** | DPG | 280 | Acetic | 720 | $H_2SO_4$ | 4.8 | | 125 | 83 # |
| 8*** | P1010 | 126 | Acetic | 840 | $H_2SO_4$ | 5.7 | | 125 | 54 |

*Polyol abreviations: DEG - diethylene glycol TTEG - tetraethylene glycol E4000 - a polyethylene glycol of avg. m.w. ca. 44004500 DPG - dipropylene glycol P1010 - a polypropylene glycol of avg. m.w. ca. 1000

**The percent is based on the weight of the total reactants.

***In these experiments only a part of the acetic acid and only 1 gram or less of $H_2SO_4$ was added initially. After some reaction had occurrred, with concurrent distillation of water, the remainder of the catalyst and reactant acids were added.

Based on a conversion of 88.5% of the dipropylene glycol.

Yield is to monoglycol esters based on the starting polyol.

It is of interest to note that formic acid, whether employed with or without catalyst ($H_2SO_4$), produced no cleavage, but only esters of the original polyglycol.

It will also be shown that polyglycerine can be treated in a similar manner to obtain glycerol triacetate or, as it is commonly known, triacetin. The following examples show the procedure and results of treating polyglycerine in this manner.

EXAMPLE 9

A quantity (1870 g) of material from a waste stream from a commercial glycerine plant consisting of about 30% polyglycerine, 10–20% of diglycerol, and the remainder consisting of up to 15% glycerol and up to 25% of other non-glycerol components, including sodium hydroxide, sodium chloride, other sodium salts, organic materials and anti-foam agent, was reacted with a total of 3045 g of acetic acid in the presence of 331 g of concentrated sulfuric acid. After 7 days there was present 360 g of diglycerol tetraacetate, and 585 g triacetin. After 10 days there was 1550 g of triacetin and less than 50 grams of the diglycerol tetraacetate.

In another experiment 200 grams of polyglycerine, 945 g of acetic acid and 92 g of concentrated sulfuric acid were reacted for 7 days. After this time the conversion was essentially 100% and the yield of triacetin was 50%.

In the following experiment acetic anhydride was employed to esterify all existing hydroxyl groups without the production of the large quantities of water which an equivalent amount of acid would have produced. Another advantage of employing the anhydride is that it reacts more rapidly with the secondary hydroxyls present in the polyglycerine and the reaction can be conducted at lower temperatures and with less of the strong acid catalyst, thus avoiding dehydration and degradation of the polyglycerine.

EXAMPLE 10

In yet another experiment, 1 liter of acetic anhydride (1080 g) was added to a refluxing solution of 700 g of polyglycerine and 990 g of acetic acid. This mixture was refluxed overnight and then 312 g of concentrated sulfuric acid and an additional 990 g of acetic acid was added and the mixture was slowly distilled for 7 days. The sulfuric acid was neutralized with sodium acetate at the end of this time, the mixture was filtered and the acetic acid was distilled from the filtrate. The residue, distilled through a Vigreux column, gave 675 g of triacetin and 100 g of diglycerol tetraacetate.

EXAMPLE 11

A column (25 mm dia. × 75 mm length) of strong acid cation exchange resin (Dowex 50) in the acid form was employed as the catalyst bed. A mixture of diethylene glycol diacetate and acetic acid was passed through the column of exchange resin at various rates and at different temperatures. Table II shows the amount of the feed converted to ethylene glycol acetates (both mon- and diacetates) together with rate, molar ratio and temperature parameters.

TABLE II

| | Mole ratio (acid/polyolester) | Feed* rate | Temp. (° C) | Percent conversion** of glycol esters total esters | mono ester |
|---|---|---|---|---|---|
| 11a | 2/1 | 154 | 117 | 20.0 | 1.5 |
| b | 2/1 | 42.2 | 117 | 34.1 | 3.9 |
| c | 2/1 | 13.6 | 117 | 44.3 | 6.2 |
| d | 2/1 | 169 | 127 | 26.0 | 2.4 |
| e | 2/1 | 16.9 | 127 | 46.8 | 6.6 |
| f | 4/1 | 12.4 | 107 | 35.3 | 2.7 |
| g | 4/1 | 9.86 | 117 | 53.8 | 6.2 |
| h | 4/1 | 11.8 | 127 | 57.6 | 7.0 |

*Grams of polyol ester/day/g resin

**It should be noted that the diester is the predominant one. If the diester is desired, the monoester can be separated and recycled. If, however, the glycol is to be recovered, the total amount recovered may be hydrolyzed.

We claim:

1. A process for obtaining di-or triesters of monomeric glycols and glycerine respectively from polyoxyalkylene glycols and polyglycerine, respectively, which comprises (A) heating at a temperature of from about 100° to about 200° C in a reactor for a period of time sufficient to produce the di-or triesters of the monomeric glycol or glycerine, respectively;

(1) one of the polyols together with (2) acetic, propionic or butyric acid in the presence of (3) a strong acid, or the acid form of a strong acid cation exchange resin, as catalyst wherein said catalyst is present in an amount greater than 4% based on total polyol and carboxylic acid (B) separating or neutralizing the acid catalyst; and (C) separating said esters of monomeric glycol or glycerine from said reaction mixture.

2. The process of claim 1 wherein the remainder of the reaction mixture apart from the esters of the monomeric glycols and glycerine is recycled to the reactor.

3. The process of claim 1 wherein the water produced in the reaction is continuously removed therefrom to cause the reactants to convert completely to the esters of monomeric glycol and glycerine.

4. The process of claim 1 wherein the catalyst employed is a strong mineral acid.

5. The process of claim 1 wherein the catalyst employed is an arylsulfonic acid.

6. The process of claim 5 wherein the arylsulfonic acid catalyst is selected from the group consisting of benzenesulfonic acid, toluenesulfonic acid and naphthalenesulfonic acid.

7. The process of claim 1 wherein the catalyst employed is the acid form of a strong acid cation exchange resin.

8. The process of claim 7 wherein the strong said cation exchange resin is a sulfonated styrene-divinylbenzene copolymer.

9. The process of claim 1 wherein the polyol employed is diethylene glycol, triethylene glycol or a higher polyethylene glycol.

10. The process of claim 1 wherein the polyol employed is dipropylene glycol, tripropylene glycol or a higher polypropylene glycol.

11. The process of claim 1 wherein the polyol employed is diglycerine, triglycerine or a higher polyglycerine.

12. The process of claim 1 wherein the hydroxyls of the polyol reactant are first esterified with acetic, propionic or butyric acid.

13. A process for obtaining monomeric polyols and glycerine from polyoxyalkylene glycols and polyglycerine, respectively, which comprises (A) heating at a temperature of from about 100° to about 200° C in a reactor for a period of time sufficient to produce the di-or triesters of the monomeric glycol or glycerine, respectively;

(1) one of the polyols together with (2) acetic, propionic or butyric acid in the presence of (3) a strong acid, or the acid form of a strong acid cation exchange resin, as catalyst wherein said catalyst is present in an amount greater than 4% based on total polyol and carboxylic acid (B) separating or neutralizing the acid catalyst, and (C) separating said esters of monomeric glycol or glycerine from said reaction mixture, and (D) hydrolyzing said esters of monomeric glycol or glycerine to form the monomeric glycol or glycerine.

14. The process of claim 13 wherein the hydroxyls of the polyol reactant are first esterified with acetic, propionic or butyric acid.

15. The process of claim 1 wherein the polyol employed is dibutylene glycol, tributylene glycol or a higher polybutylene glycol.

* * * * *

UNITED STATES PATENT AND TRADEMARK OFFICE

CERTIFICATE OF CORRECTION

PATENT NO. : 4,087,453

DATED : May 2, 1978

INVENTOR(S) : Fred A. Sherrod, William L. Howard, and Joanne D. Burger

It is certified that error appears in the above-identified patent and that said Letters Patent are hereby corrected as shown below:

Indication of the number of Claims after the Abstract should be changed from "1" to --15--.

Claim 8, after the words "wherein the strong" the word "said" should be --acid--.

Signed and Sealed this

*Tenth* Day of *October 1978*

[SEAL]

*Attest:*

RUTH C. MASON
*Attesting Officer*

DONALD W. BANNER
*Commissioner of Patents and Trademarks*